(12) United States Patent
Asashima et al.

(10) Patent No.: US 8,105,833 B2
(45) Date of Patent: Jan. 31, 2012

(54) METHOD FOR FORMING ORGAN

(75) Inventors: Makoto Asashima, Tokyo (JP); Tatsuo Hamazaki, Tokyo (JP); Hiroyuki Kagechika, Tokyo (JP); Koichi Shudo, Tokyo (JP)

(73) Assignee: Research Foundation Itsuu Laboratory, Tokyo (JP)

( * ) Notice: Subject to any disclaimer, the term of this patent is extended or adjusted under 35 U.S.C. 154(b) by 0 days.

(21) Appl. No.: 12/535,576

(22) Filed: Aug. 4, 2009

(65) Prior Publication Data

US 2009/0291492 A1    Nov. 26, 2009

Related U.S. Application Data

(63) Continuation of application No. 10/549,816, filed as application No. PCT/JP2004/003578 on Mar. 17, 2004, now abandoned.

(30) Foreign Application Priority Data

Mar. 20, 2003 (JP) ................................. 2003-077123

(51) Int. Cl.
*C12N 5/00* (2006.01)
*C12N 5/07* (2010.01)
*C12N 5/071* (2010.01)

(52) U.S. Cl. ......... 435/377; 435/354; 435/366; 435/325

(58) Field of Classification Search .................. 435/325, 435/354, 366
See application file for complete search history.

(56) References Cited

U.S. PATENT DOCUMENTS

| | | | |
|---|---|---|---|
| 5,929,069 A | 7/1999 | Shudo | |
| 6,121,256 A | 9/2000 | Shudo | |
| 6,476,017 B2 | 11/2002 | Shudo | |
| 2003/0109035 A1 | 6/2003 | Asashima et al. | |
| 2003/0191342 A1 | 10/2003 | Kagechika et al. | |
| 2005/0234130 A1 | 10/2005 | Nagai et al. | |
| 2007/0049579 A1 | 3/2007 | Nagai et al. | |
| 2009/0118264 A1 | 5/2009 | Nagai et al. | |
| 2009/0253796 A1 | 10/2009 | Nagai et al. | |

FOREIGN PATENT DOCUMENTS

| | | |
|---|---|---|
| EP | 1048659 | 11/2000 |
| EP | 1285961 | 2/2003 |
| JP | 9-100270 A | 4/1997 |
| JP | 10-59951 A | 3/1998 |
| JP | 10-114757 A | 5/1998 |
| JP | 10-237050 A | 9/1998 |
| JP | 10-338658 A | 12/1998 |
| JP | 2001-333770 | 5/2000 |
| WO | 02/096203 A1 | 12/2002 |

OTHER PUBLICATIONS

Moriya et al., Develop. Growth Differ., 2000, vol. 42, p. 593-602.*
Takahashi et al., Journal of Medicinal Chemistry, Aug. 2002, vol. 45, No. 16, p. 3327-3330.*
Kurosawa, 2007, J Bioscience and Bioengineering, vol. 103(5), pp. 389-398.*
NIH, 4 page printout from the web.*
Drysdale et al., Developmental Biology, 1997, vol. 188, p. 205-215.*
Ross et al., 1995, Histology-A Text and Atlas, 3rd Ed., Williams and Wilkins.*
Wobus et al., J. Mol. Cell Cardiol., vol. 29, pp. 1525-1539 (1997).
English Language Abstract of JP 2001-333770, (DATE).
Penny et al., Cell Biology International, vol. 26, No. 12, pp. 1057-1064 (2002).
Kobayashi et al., Gastroenterology, vol. 123, pp. 1331-1340 (2002).
Jonk et al. Mechanisms of Development.., vol. 36, pp. 165-172 (1992).
Sewter C.P. et al., "Regional Differences in the Response of Human Pre-Adipocytes to PPARγ and RXRα Agonists", Diabetes (2002), vol. 51, No. 3, pp. 718-723.
Kim M.J. et al., "Limited Cooperation between Peroxoisome Proliferator-Activated Receptors and Retinoid X Receptors Agonists in Sebocyte Growth and Development", Molecular Genetics and Metabolism (2001), vol. 74, No. 3, pp. 362-369.
Million K. et al., "Effects of Retinoic Acid Receptor-Selective Agonists on Human Nasal Epithelial Cell Differentiation" American Journal of Respiratory Cell and Molecular Biology (2001), vol. 25, No. 6, pp. 744-750.
Shibakura M. et al., "A Retinoic Acid Receptor-α (RARα) Selective Agonist Modulates Procoagulant Activity of Acute Promyelocytic Cells and Induces Their Differentiation Into Neutrophils", Blood (1998), vol. 91, No. 2, pp. 724-725.
Weston A.D. et al., "Regulation of Skeletal Progenitor Differentiation by the BMP and Retinoid Signaling Pathways", The Journal of Cell Biology (2000), vol. 148, No. 4, pp. 679-690.

(Continued)

*Primary Examiner* — Peter Paras, Jr.
*Assistant Examiner* — David A Montanari
(74) *Attorney, Agent, or Firm* — Greenblum & Bernstein, PLC

(57) ABSTRACT

A method for forming an organ and/or tissue from undifferentiated cells derived from a vertebrate animal in vitro, which comprises the step of culturing the undifferentiated cells derived from a vertebrate animal in the presence of a retinoic acid X receptor ligand (e.g., a retinoic acid X receptor agonist or antagonist), and a method for forming a pancreas from undifferentiated cells derived from a vertebrate animal in vitro or a method for forming a tissue having morphology and function of a pancreas from undifferentiated cells derived from a vertebrate in vitro, which comprises the step of culturing the undifferentiated cells derived from a vertebrate animal in the presence of a retinoic acid receptor ligand, together with activin, that does not substantially bind to the retinoic acid receptor subtype γ.

3 Claims, 4 Drawing Sheets

OTHER PUBLICATIONS

Nagy L. et al., "Activation of Retinoid X Receptors Induces Apoptosis in HL-60 Cell Lines", Molecular and Cellular Biology (1995), vol. 15, No. 7, pp. 3540-3551.
Ishida S. et al., "Clinically Potential Subclasses of Retinoid Synergists Revealed by Gene Expression Profiling", Molecular Cancer Therapeutics (2003), vol. 2, No. 1, pp. 49-58.
Takahashi B. et al., "Novel Retinoid X Receptor Antagonists: Specific Inhibition of Retinoid Synergism in RXR-RAR Heterodimer Actions", Journal of Medicinal Chemistry (2002), vol. 45, No. 16, pp. 3327-3330.
Honda M. et al., "RXR agonist enhances the differentiation of cardiomyocytes derived from embryonic stem cells in serum-free conditions", Biochemical and Biophysical Research Communications (2005), vol. 333, No. 4, pp. 1334-1340.
Collins S.J., "The HL-60 Promyelocytic Leukemia Cell Line: Proliferation, Differentiation, and Cellular Oncogene Expression", Blood (1987), vol. 70, No. 5, pp. 1233-1244.
Montesano R. et al., "Retinoids induce lumen morphogenesis in mammary epithelial cells", Journal of Cell Science (2002), vol. 115, No. 23, pp. 4419-4431.
Raz Y. et al. "Retinoic Acid Signaling is Necessary for the Development of the Organ of Corti", Developmental Biology (1999), vol. 213, No. 1, pp. 180-193.
Tran C.M. et al., "The RXRα gene functions in a non-cell-autonomous manner during mouse cardiac morphogenesis", Development (1998), vol. 125, No. 10, pp. 1951-1956.
U.S. Appl. No. 11/366,454 to Nagai et al., filed Mar. 3, 2006 and entitled "Medicament Having Promoting Action on Neovascularization".
U.S. Appl. No. 10/549,816, filed Mar. 17, 2004, Asashima et al.
Koch, S.S.C. et al. "Synthesis of Retinoid X Receptor-Specific Ligands That Are Potent Inducers of Adipogenesis in 3T3-L1 Cells," Journal of Medicinal Chemistry, vol. 42, pp. 742-750 (1999).
Sucov, H.M. et al. "RXRα mutant mice establish a genetic basis for vitamin A signaling in heart morphogenesis," Genes & Development, vol. 8, No. 9, pp. 1007-1018 (1994).
Costa, S.L. et al. "Effects of a novel synthetic retinoid on malignant glioma in vitro: inhibition of cell proliferation, induction of apoptosis and differentiation," European Journal of Cancer, vol. 37, pp. 520-530 (2001).
English Language Abstract of JP 9-100270 A, 1997.
English Language Abstract of JP 10-338658 A, 1998.
English Language Abstract of JP 10-59951A, 1998.
English Language Abstract of JP 10-114757A, 1998.
English Language Abstract of JP 10-237050 A, 1998.
Minucci et al., Molecular & Cellular Biology, 1997, vol. 17, No. 2, p. 644-655.
Moriya et al., Develop. Growth Differ., 2000, vol. 42, p. 593-602.
Neuville et al., Arterioscler. Thromb. Vasc. Biol., 1999, vol. 19, p. 1430-1436.
Medical Dictionary online (Mar. 11, 2008) ectoderm definition.
Fontana et al., PNAS 1981, vol. 78 No. 6 p. 3863-3866.

* cited by examiner

METHOD FOR FORMING ORGAN

CROSS-REFERENCE TO RELATED APPLICATIONS

This application is a continuation of Application No. 10/549,816, now abandoned, which is a national stage of PCT/JP2004/003578, filed Mar. 17, 2004, which claims priority to Japanese Application No. 2003-077123, filed Mar. 20, 2003. The disclosures of Application No. 10/549,816 and PCT/JP2004/003578 are incorporated by reference herein in their entireties.

TECHNICAL FIELD

The present invention relates to a method for forming an organ from undifferentiated cells derived from a vertebrate.

BACKGROUND ART

A huge numbers of organs and tissues exist in a living body of vertebrates including a human. The organs and tissues are originally formed from a single fertilized egg by undergoing cell division (cleavage) and cell differentiation, and finally constitute an individual body with a well-balanced system. Processes for the formation of organs and tissues are highly complicated, through which important intercellular interactions called induction phenomena are considered to be involved in multiple steps.

Attempts have been made for in vitro reproduction of the organ formation processes occurring in vivo to form a desired organ from undifferentiated cells (see, for example, "Organ formation from undifferentiated cells", Inflammation/Regeneration, Vol. 22, 21, 2002 as well as Japanese Patent Unexamined Publication (Kokai) Nos. 2001-299335 and 2001-333770 for organ formation of pancreas). For example, when animal cap cells (pluripotent cell aggregates) of *Triturus pyrrhogaster* at the blastula stage as undifferentiated cells are treated with activin at a high concentration, a rhythmically beating heart can be formed in a formation rate of 60%. The resulting heart can maintain a normal number of beats even for one month or longer, and gene expression specific to cardiomyocytes, existence of an intercalated disc specific to cardiac muscles and the like can also be observed. Therefore, the heart is considered to a substantially complete heart from viewpoints of function and structure.

Retinoic acid (vitamin A acid) is an active metabolite of vitamin A and has extremely important physiological actions such as an action of differentiating immature cells under development to mature cells having a peculiar function, cell growth promoting action and a life-supporting action. Various vitamin A derivatives having been synthesized so far, e.g., benzoic acid derivatives described in Japanese Patent Unexamined Publication (Kokai) Nos. 61-22047 and 61-76440, compounds described in Journal of Medicinal Chemistry, 1988, Vol. 31, No. 11, p. 2182 and the like, have also been elucidated to have similar physiological actions. Retinoic acid and the aforementioned compounds having retinoic acid-like biological activities are generically referred to as "retinoids."

It is known that retinoic acid is a regulatory factor for the embryonic patterning along the anteroposterior axis (Nature, 340, 140-144, 1989; Development, 112, 945-958, 1991; Dev. Biol., 192, 1-16, 1997; Zool. Sci., 15, 879-886, 1998), and that the retinoic acid transforms the anterior neural tissue of *Xenopus* embryo to a posterior one and is effective on mesodermal development (Genes Dev., 5, 175-187, 1991; Develop. Growth. Differ., 35, 123-128, 1993). It has also been reported that treatment with activin can induce most of mesodermal tissues such as notochord, muscle, mesenchyme and coelomic epithelium dose-dependently in *Xenopus* animal cap cells (Roux's Arch. Dev. Biol., 198, 330-335, 1990; Nature, 347, 391-394, 1990; Roux's Arch. Dev. Biol., 200, 230-233, 1991), and changing the dosage of retinoic acid that is used for co-treatment with activin enables the mesodermal tissues such as notochord, muscle and pronephros differentiated from animal cap cells to be lateralized and posteriorized (Develop. Growth. Differ., 35, 123-128, 1993).

As for the action of retinoic acid on the endodermal organ, it has been reported by Dixon et al. that when *Xenopus* embryos at developmental stages 22 to 32 are treated with retinoic acid, the morphology of digestive organs such as the intestines, liver and stomach becomes abnormal. However, it has also been reported that the pancreas of *Xenopus* embryos at developmental stages 22 to 32 treated with retinoic acid is formed normally, and no influence is found in the expression of XlHbox8, an endoderm-specific marker (Dev. Genes Evol., 208, 318-326, 1998).

It has also been revealed that all-trans retinoic acid binds to a retinoic acid receptor (RAR) belonging to the intranuclear receptor superfamily (Evans, R. M., Science, 240, p. 889, 1988), which exists in the cell nucleus, as a ligand to regulate growth/differentiation or death of animal cells (Petkovich, M., et al., Nature, 330, pp. 444-450, 1987). It is known that pancreas can be formed in vitro by using the all-trans retinoic acid or using all-trans retinoic acid and activin in combination (Japanese Patent Unexamined Publication (Kokai) Nos. 2001-299335 and 2001-333770).

As for the expression of the physiological activities of retinoic acid, existence of retinoid X receptors (RXRs, binding to 9-cisretinoic acid as a natural ligand (this compound is also serve as a ligand of RARs)) has been verified. It has been elucidated that RXR forms a dimer with RAR to induce or suppress gene transcription and thereby regulate the expression of the physiological activities of retinoic acid (Mangelsdorf, D. J. et al., Nature, 345, pp. 224-229). Various agonists or antagonists that can bind to RXRs are known (examples of the agonists include HX600 described in Japanese Patent Unexamined Publication (Kokai) No. 1'-59951 and the like, and examples of the antagonists include HX603 described in the same publication and the like). However, whether or not an organ can be formed from undifferentiated cells by using a ligand that binds to RXR has not yet been known so far.

DISCLOSURE OF THE INVENTION

An object of the present invention is to provide a method of forming a desired organ from undifferentiated cells derived from a vertebrate. The present inventors have conducted various studies to achieve the foregoing object, and as a result, they found that an organ such as a heart and a nerve can be formed from undifferentiated cells by using a ligand that binds to an RXR. Further, they found that when an RAR ligand, which does not substantially bind to the retinoic acid receptor (RAR) subtype γ as an RAR ligand, are used together with activin, a highly differentiated pancreas can be formed from undifferentiated cells. The present invention was achieved on the basis of these findings.

The present invention thus provides a method for forming an organ and/or tissue from undifferentiated cells derived from a vertebrate in vitro, which comprises the step of culturing the undifferentiated cells derived from a vertebrate in the presence of a retinoic acid X receptor ligand. According to preferred embodiments, the present invention provides the aforementioned method, wherein the retinoic acid X receptor ligand is an agonist or antagonist of the retinoic acid X receptor, and the aforementioned method, wherein the organ and/or tissue to be formed is a heart, a smooth muscle tissue, or an adipocyte tissue. The present invention also provides a differentiation inducer for forming an organ and/or a tissue from undifferentiated cells derived from a vertebrate in vitro, which comprises a retinoic acid X receptor ligand.

From another aspect, the present invention provides a method for forming a pancreas from undifferentiated cells derived from a vertebrate in vitro or a method for forming a tissue having morphology and function of a pancreas from undifferentiated cells derived from a vertebrate in vitro, which comprises the step of culturing the undifferentiated cells derived from a vertebrate in the presence of a retinoic acid receptor ligand that does not substantially bind to the retinoic acid receptor subtype γ together with activin. According to a preferred embodiment of this invention, there is provided the aforementioned method, wherein the aforementioned retinoic acid receptor ligand is 4-[(5,6,7,8-tetrahydro-5,5,8,8-tetramethyl-2-naphthalenyl)carbamoyl]benzoic acid. The present invention also provides a differentiation inducer for forming a pancreas or tissue having morphology and function of a pancreas from undifferentiated cells derived from a vertebrate in vitro, which comprises a retinoic acid receptor ligand that does not substantially bind to the retinoic acid receptor subtype γ.

From further aspect, the present invention also provides an organ and/or issue formed by the aforementioned methods.

BEST MODE FOR CARRYING OUT THE INVENTION

Figure 1:
FIG. 1 is a photograph showing ES cell colonies.

In the present specification, the term "organ and/or tissue" means any of organs, tissues, and bound masses thereof for constituting a vertebrate animal. For example, a structure ordinarily classified as a tissue may bind to an organ formed by the method of the present invention, and a method for forming the bound mass and the like also falls within the scope of the present invention. Further, the organ and tissue simultaneously formed by the method of the present invention may each consist of two or more types of organs and tissues. Examples of the organ include, for example, heart, pancreas, kidney and the like. Examples of the tissue include nerve tissue, smooth muscle tissue, adipocyte tissue and the like. However, the organ and tissue are not limited to these examples. Preferred examples of the organ include heart, pancreas and the like, and preferred examples of the tissue include smooth muscle tissue, adipocyte tissue and the like.

The retinoic acid X receptor ligands (hereinafter also referred to as "RXR ligands") include a retinoic acid X receptor agonist (hereinafter also referred to as "RXR agonist") and retinoic acid X receptor antagonist (hereinafter also referred to as "RXR antagonist"). Whether or not a substance can serve as an RXR ligand can be easily confirmed by those skilled in the art by, for example, the methods described in Boehm, M. F. et al., J. Med. Chem., 37(18), 2930-2941, 1994; Heyman, R. A. et al., Cell, 68(2), 397-406, 1992; Levin, A. A. et al., Nature, 355 (6358), 359-361, 1992; Chen, J. Y. et al., Nature, 382, 819-822, 1996 and the like. As the RXR ligand, compounds that can act as an RXR ligand among those described in, for example, Japanese Patent Unexamined Publication (Kokai) Nos. 9-100270, 10-59951, 10-114757, 10-237050, 10-338658 and 2000-273079, International Patent Publication WO99/24415 and the like can be used. However, the RXR-ligands are not limited to these compounds. Two or more types of RXR ligands may be used in combination. The RXR agonist and RXR antagonist can also be used in combination.

More specifically, examples of the RXR agonist include, for example:
4-[5H-2,3-(2,5-dimethyl-2,5-hexano)-5-methyldibenzo[b,e][1,4]diazepin-11-yl]benzoic acid (HX600);
4-[2,3-(2,5-dimethyl-2,5-hexano)dibenzo[b,f][1,4]thiazepin-11-yl]benzoic acid (HX630);
4-[2,3-(2,5-dimethyl-2,5-hexano)dibenzo[b,e]azepin-11-yl]benzoic acid (HX640);
4-[1,3-dihydro-7,8-(2,5-dimethyl-2,5-hexano)-1-methyl-2-oxo-2H-1,4-benzodiazepin-5-yl]benzoic acid (HX801);
(Z)-5-[4-[N-methyl-(5,6,7,8-tetrahydro-5,5,8,8-tetramethyl-naphthalen-2-yl)carboxamido]benzylidene]-2,4-thiazolidinedione (TZ191);
(Z)-5-[4-[N-methyl-N-(5,6,7,8-tetrahydro-3,5,5,8,8-pentamethylnaphthalen-2-yl)amino]benzylidene]-2,4-thiazolidinedione (TZ335);
4-[N-cyclopropylmethyl-N-(6,6,7,8-tetrahydro-3,5,6,8,8-pentamethylnaphthalen-2-yl)amino]benzoic acid (DA124);
2-[N-cyclopropylmethyl-N-(5,6,7,8-tetrahydro-5,5,8,8-tetramethylnaphthalen-2-yl)amino]pyrimidine-5-carboxylic acid (PA024);
4-[1-(5,6,7,8-tetrahydro-5,5,8,8-tetramethylnaphthalen-2-yl)-1,3-dioxolan-1-yl]benzoic acid (SR11237);
4-[1-(5,6,7,8-tetrahydro-3,5,5,8,8-pentamethylnaphthalen-2-yl)ethen-1-yl]benzoic acid (LGD 1069);
6-[1'-(5,6,7,8-tetrahydro-3,5,5,8,8-pentamethylnaphthalen-2-yl)cycloprop-1-yl]pyridine-3-carboxylic acid (LG268) and the like.

Examples of the RXR antagonist include:
4-(5H-2,3-(2,5-dimethyl-2,5-hexano)-5-methyl-8-nitrodibenzo[b,e][1,4]diazepin-11-yl)benzoic acid (HX531);
4-[5H 2,3-(2,5-dimethyl-2,5-hexano)-5-n-propyldibenzo[b,e][1,4]diazepin-11-yl]benzoic acid (HX603);
4-(5H-10,11-dihydro-2,3-(2,5-dimethyl-2,5-hexano)-5,10-dimethyl-8-phenyldibenzo[b,e][1,4]diazepin-11-yl)benzoic acid (HX711);
2-[N-(3-n-hexyloxy-5,6,7,8-tetrahydro-5,5,8,8-tetramethyl-naphthalen-2-yl)-N-methylamino]pyrimidine 5-carboxylic acid (PA452);
5-[4-(5,6,7,8-tetrahydro-5,5,8,8-tetramethylnaphthalen-2-yl)phenyl]tropolone (Tp 180);

(2E,4E,6Z)-3-methyl-7-(5,6,7,8-tetrahydro-5,5,8,8-tetramethyl-3-n-propyloxynaplhthalen-2-yl)octa-2,4,6-trienoic acid (LG100754);

4-[N-[3-(2-ethyl-o-carboran-1-yl)phenyl]-N-methylamino] benzoic acid and the like. However, the RXR agonist and RXR antagonist are not limited to these specific compounds.

Types of undifferentiated cells derived from a vertebrate animal that can be used for the method of the present invention are not particularly limited, and undifferentiated cells derived from vertebrates such as birds, reptiles, and amphibians in addition to mammals can be used. As the undifferentiated cells, stem cells such as embryonic stem cells, hematopoietic stem cells, and basal cells of small intestine crypts, as well as cell populations such as animal cap cells and embryoid bodies of mid-blastula to late-blastula, for example, can be used. The term "undifferentiated cells" used in the present specification should not be construed to exclude a cell population and cell aggregate formed by two or more kinds of cells.

Formation of an organ and/or tissue by the method of the present invention can be carried out by various methods used in this field as methods of forming organs and/or tissues from undifferentiated cells. For example, methods of forming a pancreas from undifferentiated cells are described in detail in Japanese Patent Unexamined Publication (Kokai) Nos. 2001-299335 and 2001-333770, and accordingly, those skilled in the art can form a desired organ from undifferentiated cells according to the methods of the examples in the present specification by referring to the aforementioned publications. The entire disclosures of Japanese Patent Unexamined Publication (Kokai) Nos. 2001-299335 and 2001-333770 are incorporated in the disclosures of the present specification by reference.

For example, an organ can be formed by culturing embryoid bodies induced from embryonic stem cells in the presence of an RXR ligand at a suitable concentration for one to several days. After the embryoid bodies are cultured in the presence of the RXR ligand for one to several days, culture may be further continued in the absence of the RXR ligand. The concentration of the RXR ligand is not particularly limited, and can be suitably selected from the range of, for example, from about $1 \times 10^{-12}$ to $1 \times 10^{-3}$ M. The method of the present invention can be carried out in vitro, and the term. "in vitro" is used in the present specification to mean outside the living organisms and should not be construed in any limitative sense.

As embryonic stem cells (ES cells), for example, the E14 cells of the 129 mouse strain established by Hooper-(ATCC #: CRL-1821), B6 cells of the C57BL mouse strain established by Ledermann and Burki (ATCC #: SCRC-1002) and the like can be used. These cells were established as cell lines from internal cell aggregates in the mouse blastocyst. However, the types of ES cells are not limited to these examples. The passage number of ES cells usually does not affect the organ and/or tissue forming ability.

For example, embryoid bodies induced from ES cells are adhered to a gelatin-coated culture plate, and an RXR ligand solution diluted with a medium as required is added to the medium to treat the embryoid bodies for one to several days. As a solvent for dissolving the RXR ligand, water, physiological saline, or a buffer as well as an organic solvent such as dimethyl sulfoxide or a mixture of water and an organic solvent can be used. To culture embryoid bodies, a multiwell plate coated with laminin, collagen I, or matrigel (Biocoat, Becton Dickinson) can also be used. After this treatment, it is preferable to record the cell differentiation state after a predetermined time period. Before or after the aforementioned treatment, the embryoid bodies may also be treated with BMP2/4 or BMP6/7, which are bone formation factors (bone morphogenic proteins, BMP), as well as induction factors such as FGF, activin, follistatin, vitellogenin, insulin, glucagon, concanavalin, cytochalasin and cadverine, cell growth factors, cytokines and the like. The direction and rate of formation of organ and/or tissue rate may be improved by applying the treatment as mentioned above and the like.

The method of the present invention provided from another aspect is a method for forming a pancreas from undifferentiated cells derived from a vertebrate animal in vitro, or a method for forming a tissue having morphology and function of pancreas from undifferentiated cells derived from a vertebrate animal in vitro, which comprises the step of culturing the undifferentiated cells of a vertebrate in the presence of a retinoic acid receptor ligand, together with activin, that does not substantially bind to the retinoic acid receptor subtype γ.

The retinoic acid receptor (RAR) ligand (hereinafter also referred to as "RAR ligand") is a compound that has a property of binding to a receptor necessary for all-trans-retinoic acid or 9-cis-retinoic acid to exhibit the physiological actions. For the method of the present invention, an RAR ligand that exhibits actions similar to those of retinoic acid (for example, one or more kinds of actions among cell differentiation action, cell growth promoting action, life-supporting action and the like) or a part of the actions can be preferably used as the retinoic acid receptor agonist (hereinafter also referred to as "RAR agonist"). Whether or not a substance is the RAR ligand can be easily determined by various methods described in M. Sporn et al., Retinoids, Academic Press, 1984. The RAR ligand used for the method of the present invention is an RAR ligand that binds to the RAR subtype α (RAR α) and subtype β (RAR β) and does not substantially bind to the subtype γ (RAR γ). Binding to a retinoic acid receptor subtype can be easily confirmed by methods described in the literature (H. de The and A. Dejean, "Retinoids, 10 years on", Basel, Karger, pp. 2-9, 1991).

As the RAR ligand having the aforementioned properties, for example, an RAR agonist comprising phenyl-substituted carbamoylbenzoic acid or phenyl-substituted carboxamidobenzoic acid as the basal skeleton can be used. Various RAR ligands having phenyl-substituted carbamoylbenzoic acid or phenyl-substituted carboxamidobenzoic acid as their basal skeleton are known. The term "basal skeleton" means a fundamental chemical structure for binding of one or more arbitrary substituents. It is usually preferred that a phenyl group substituted on carbamoyl group or carboxamido group has one or more substituents. As the substituents, for example, a lower alkyl group can be used (in the present specification, the term "lower" means a carbon number of about 1 to 6, preferably 1 to 4). The lower alkyl group is preferably a straight or branched alkyl group, and more specifically, examples thereof include methyl group, ethyl group, n-propyl group, isopropyl group, n-butyl group, sec-butyl group, tert-butyl group and the like.

Further, examples of the substituent on the aforementioned phenyl group include a lower alkoxy group such as methoxy group, a halogen atom (the halogen atom may be any of fluorine atom, chlorine atom, bromine atom and iodine atom), a lower alkyl-substituted silyl group such as trimethylsilyl group and the like. Preferred examples of the phenyl group substituting on the carbamoyl group include a phenyl group substituted with two to four lower alkyl groups, a phenyl group substituted with one or two tri(lower alkyl)silyl groups and the like, and more preferred examples include a phenyl group substituted with two to four alkyl groups, a phenyl group substituted with two trimethylsilyl groups and the like.

If the two lower alkyl groups substituting on the aforementioned phenyl group are adjacent to each other, these two lower alkyl groups may form one or two, preferably one, 5- or 6-membered rings together with the ring-constituting carbon atoms of the phenyl group to which they bind. The ring formed as described above may be saturated or unsaturated, and may be substituted with one or more lower alkyl groups such as methyl group and ethyl group on the ring. On the formed ring mentioned above, two to four methyl groups, more preferably four methyl groups, may substitute. For example, it is preferred that two adjacent lower alkyl groups substituting on the phenyl ring together form 5,6,7,8-tetrahydronaphthalene ring, 5,5,8,8-tetramethyl-5,6,7,8-tetrahydronaphthalene ring or the like.

Preferred examples of the RAR ligand include an RAR ligand represented by the following general formula (I):

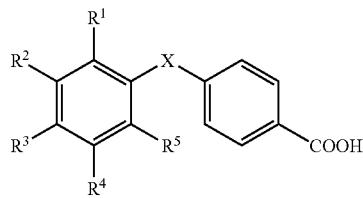

[wherein $R^1$, $R^2$, $R^3$, $R^4$, and $R^5$ each independently represent hydrogen atom, a lower alkyl group or a lower alkyl-substituted silyl group, wherein when any two adjacent groups among $R^1$, $R^2$, $R^3$, $R^4$ and $R^5$ are lower alkyl groups, they may form a 5- or 6-membered ring together with the carbon atoms of the benzene ring to which they bind (this ring may have one or more alkyl groups), and X represents —CONH— or —NHCO—].

In the aforementioned general formula (I), as the lower alkyl group represented by $R^1$, $R^2$, $R^3$, $R^4$ or $R^5$, a straight or branched alkyl group having about 1 to 6 carbons, preferably 1 to 4 carbons, can be used. For example, methyl group, ethyl group, n-propyl group, isopropyl group, n-butyl group, sec-butyl group, tert-butyl group and the like can be used. One or more arbitrary substituents may exist on the aforementioned lower alkyl group. Examples of the substituent include hydroxyl group, a lower alkoxy group, a halogen atom and the like. Examples of the lower alkyl-substituted silyl group represented by $R^1$, $R^2$, $R^3$, $R^4$ or $R^5$ include, for example, trimethylsilyl group and the like.

Two of adjacent lower alkyl groups selected from the group consisting of $R^1$, $R^2$, $R^3$, $R^4$ and $R^5$ may form one or two, preferably one 5- or 6-membered ring, together with the carbon atoms of the benzene ring to which they bind. The ring formed as described above may be saturated, partially saturated or aromatic, and may have one or more alkyl groups on the ring. As the alkyl group that can substitute on the ring, a straight or branched alkyl group having about 1 to 6 carbon atoms, preferably 1 to 4 carbon atoms, can be used. For example, methyl group, ethyl group and the like can be used, and preferably two to four methyl groups, more preferably four methyl groups, may substitute. For example, it is preferred that 5,6,7,8-tetrahydronaphthalene ring, 5,5,8,8-tetramethyl-5,6,7,8-tetrahydro naphthalene ring or the like is formed by the benzene ring on which $R^2$ and $R^3$ substitute and $R^2$ and $R^3$.

More specifically, examples of the RAR ligand suitably used for the method of the present invention include 4-(3,5-bis (trimethylsilyl) phenylcarboxamide) benzoic acid (Am555s, J. Med. Chem., 33, pp.1430-1437, 1990), 4-[(5,6,7,8-tetrahydro-5,5,8,8-tetramethyl-2-naphthalenyl)carbamoyl]benzoic acid (Am80, Hashimoto, Y., Cell struct. Funct., 16, pp.113-123, 1991; Hashimoto, Y. et al., Biochem. Biophys. Res. Commun., 166, pp.1300-1307, 1990) and the like, and a particularly preferred RAR ligand is Am80.

The method of the present invention comprises the step of culturing undifferentiated cells derived from a vertebrate animal in the presence of the aforementioned RAR ligand and activin. As the undifferentiated cells and the culture method, those explained above can be used. The method of the present invention has a feature, for example, in that an organ substantially completed as a pancreas or a highly differentiated tissue substantially having morphology and function of pancreas can be obtained without using any induction factor (for example, FGF) other than activin. The concentrations of the RAR ligand and activin used in combination can be suitably selected. For example, the concentration of the RAR ligand can be selected from a range of about $1 \times 10^{-12}$ to $1 \times 10^{-3}$ M, and the concentration of activin can be selected from a range of about 0.1 to 1000 ng/ml. Further, an RAR ligand and an RXR ligand can be used in combination to form an organ having a more complicated structure.

The organ and/or tissue formed by the method of the present invention can be used for screening of a medicament that acts on that organ and/or tissue as a direct or indirect site of action. For example, when a heart is formed by the method of the present invention, the formed heart has constant beating rhythm over a long period of time, and by using the resulting heart, a medicament that acts on increase or decrease of heart rate, for example, can be screened.

EXAMPLES

The present invention will be more specifically explained with reference to the examples. However, the scope of the invention will not be limited to these examples.

Example 1

Formation of Heart Using RXR Ligand

As ES cells, E 14 cells of the 29 mouse strain (ATCC #: CRL-1821) or B6 cells of the C57BL mouse strain (ATCC #: SCRC-1002) were used. Mouse fetal fibroblasts prepared from a mouse embryo on the 13th day were inoculated on a 0.1% gelatin-coated culture dish, and cultured in a medium containing 12% fetal bovine serum (Gibco), 100 U/ml penicillin (Sigma) and 100 μg/ml streptomycin (Sigma) for 24 hours. These cells were treated with 10 μg/ml mytomicin C (MMC, Sigma) for four hours to inhibit cell division and then washed twice with phosphate-buffered saline (PBS) to remove MMC. The ES cells were inoculated on these fibroblasts (feeder). As the medium for the ES cells, D-MEM (high glucose, Gibco) containing 15% fetal bovine serum for ES (Gibco), 2 mM L-glutamine (Gibco), MEM non-essential amino acid (Sigma), 1 mM sodium pyruvate (Gibco), 0.0007% β-mercaptoethanol (Sigma), 1000 U/ml Leukemia inhibiting factor (Chemicon), 100 U/ml penicillin (Sigma) and 100 μg/ml streptomycin (Sigma) was used, and the cells were cultured in a $CO_2$ incubator (5% $CO_2$, 100% humidity) at 37° C. The medium was exchanged every day.

Figure 2:
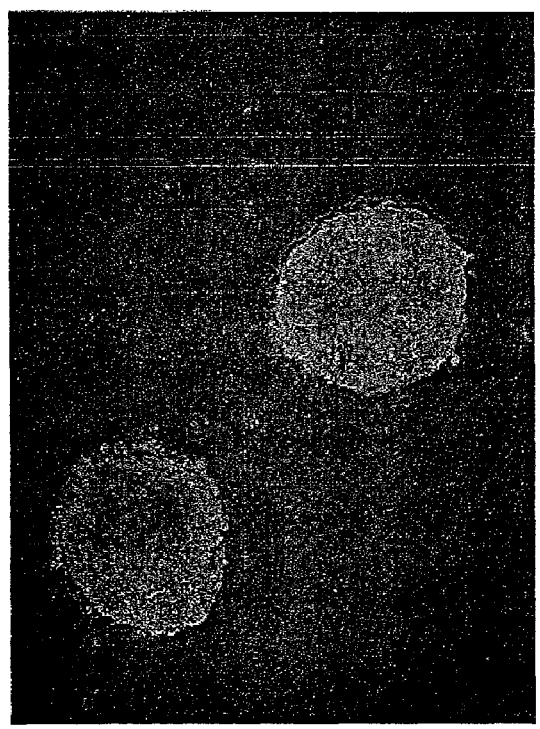
FIG. 2 is a photograph showing embryoid bodies formed on a bacteria dish.

Subculture was performed 72 hours after the inoculation of the ES cells. MMC-treated feeder cells (mouse fetus fibroblasts) were inoculated on a gelatin-coated culture dish, and after 24 hours, the ES cells completely dissociated by a treatment with 0.05% trypsin-0.02% EDTA were inoculated to allow formation of colonies (see, FIG. 1). The ES cells were cultured for three days after the inoculation to allow formation of colonies, and a colony was isolated by pipetting and then inoculated on a culture dish for bacteria with an extremely low cell attachment property. As the medium, D-MEM (high glucose) containing 15% Knockout SR (KSR, Gibco), 100 U/ml penicillin and 100 μg/ml streptomycin was used. The cells were further cultured for three days under this condition to prepare embryoid bodies (FIG. 2).

Figure 3:
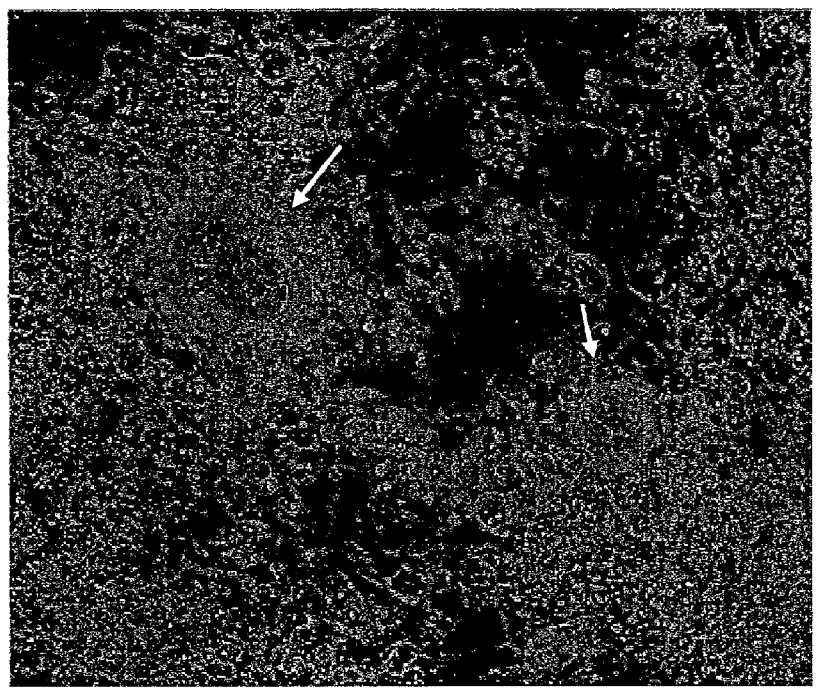
FIG. 3 is a photograph showing a heart (cardiac muscle-like cell aggregates) formed by the method of Example 1.

Four to six of the embryoid bodies were inoculated on a 0.1% gelatin-coated 24-well plate (TPP), added with $L \times 10^{-5}$ M PA024 (2-[N-cyclopxopylmethyl-N-(5,6,7,8-tetrahydro-5,5,8,8-tetramethylnaphthalen-2-yl)aminopyrimidine-5-carboxylic acid) as the RXR ligand and cultured for 2 days. Defining the start of the treatment as 0 hour, autonomically beating cardiac muscle-like cell aggregates were formed after 48 to 72 hours (FIG. 3). The frequency of appearance of this cell aggregate was 0.2 cell aggregate per embryoid body, and almost no differentiation of cardiac muscle-like cells was observed in the untreated group or the control group treated with $1 \times 10^{-5}$ M all-trans retinoic acid over two weeks after the treatment, which suggested significant action of PA024. Embryoid bodies treated with $2 \times 10^{-6}$ M PA024 produced cardiac muscle-like cell aggregates at a high frequency, although the time of appearance was delayed, and the formation of 0.5 cell aggregate per embryoid body was observed in 72 to 96 hours. These cell aggregates were formed without a fibrous structure observed in skeletal muscle-like cells and the like, and the formed cell aggregates continued autonomous beating.

Example 2

Formation of Smooth Muscle and Adipocytes Using RXR Ligand

Figure 4:
FIG. 4 is a photograph showing a smooth muscle tissue (smooth muscle-like cell aggregates) formed by the method of Example 2.
Figure 5:
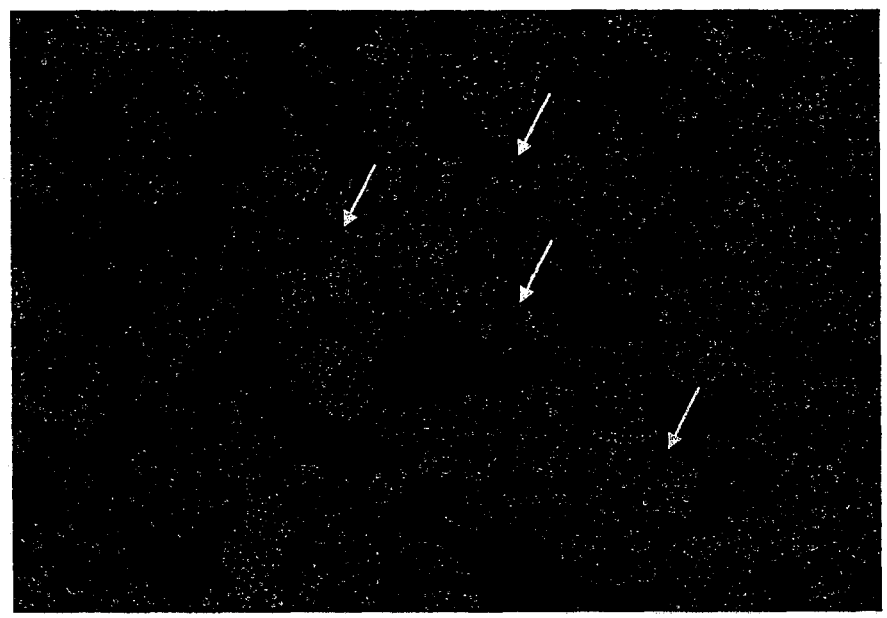
FIG. 5 is a photograph showing an adipocyte tissue formed by the method of Example 2.

When the embryoid bodies were treated with $1 \times 10^{-5}$ to $2 \times 10^{-6}$ M PA024 and then further cultured in the same manner as in Example 1, smooth muscle-like cells were formed in about one to two weeks. The resulting cell aggregate showed slow peristalsis. The frequency of appearance was 0.1 to 0.2 cell aggregate per embryoid body (FIG. 4). Further, appearance of adipocytes was observed in about two weeks, and after the culture was continued for 20 days, about 30 to 40% of the total cells became adipocytes, which was substantially 100% in terms of the value per embryoid body. In comparison with the control group (treated with $1 \times 10^{15}$ M all-trans retinoic acid), two or three times more adipocytes were formed in the PA024 treated group (FIG. 5).

Example 3

Formation of Pancreas Using Combination of Am80 as RAR Ligand and Activin

Primary mouse embryonic fibroblasts (PMEFs), of which cell division was inhibited by treatment with Mytomicin-C (10 μg/ml, 3 hours), were inoculated on a 10-cm culture dish (TPP) coated overnight with 0.1% gelatin, cultured for more than one day and used as a feeder layer. The ES-E14TG2a cells (ATCC # CRL-1821), which are widely used as mouse ES cells, were inoculated on the feeder layer and cultured. As the medium for ES cells, DMEM (high glucose, Gibco) containing 15% fetal bovine serum (FBS, Gibco), non-essential amino acid, 0.007% β- mercaptoethanol, 1000 U/ml Leukemia inhibiting factor (Chemicon), 100 U/ml penicillin, and 0.1 mg/ml streptomycin was used. The medium was exchanged every day.

EBs were formed from colonies 72 hours after the inoculation of the ES cells. ES cell colonies were washed once with Dulbecco's PBS, then added with 1 ml of 1 mg/ml collagenase/dispase (Roche) per 10-cm dish and treated at room temperature for 30 to 40 seconds. At when about 50% of the colonies floated in the solution, 13 ml of DMEM (high glucose) containing Embryoid medium (EM), 15% Knockout Serum Replacement (KSR, Gibco), 100 U/ml penicillin, and 0.1 mg/ml streptomycin was added to each 10-cm culture dish, and the colonies were collected. ES cell colonies were collected with the medium into a 15 ml tube so as not to physically damage the colonies and left standing for about 5 minutes. When colonies precipitated, the medium was removed, and the colonies were resuspended in EM. These ES colonies were inoculated on a 10-cm low-attachment culture dish (Corning or Nunc), and the culture was continued as a floating system. The medium was exchanged every other day, and the cells on the 4th day were used for experiment as the embryoid bodies (EBs).

After 96 hours from the start of the formation of EBs, one EB of about 500 μm in diameter was transferred to each well of a low attachment 24-well plate (Corning or Nunc) with 100 μl of medium under observation using a stereoscopic microscope. Then, EBs were added with 900 μl of a differentiation inducing medium containing activin/Am80 (4-[(5,6,7,8-tetrahydro-5,5,8,8-tetramethyl-2-naphthalenyl)carbamoyl] benzoic acid): DMEM (high glucose) containing 15% KSR, 10 ng/ml activin, 0.1 μM Am80, 0.1% BSA, 100 U/ml penicillin, and 0.1 mg/ml streptomycin, and the culture was continued for 48 hours.

EBs were treated in the differentiation inducing medium for 48 hours (6 days after formation of EBs), then transferred to a 24-well tissue culture dish coated overnight with 0.1% gelatin (TPP) under observation using a stereoscopic microscope and cultured in DMEM (high glucose) containing 10% KSR, 100 U/ml penicillin and 0.1 mg/ml streptomycin with exchanging the medium once in three days.

Figure 6:
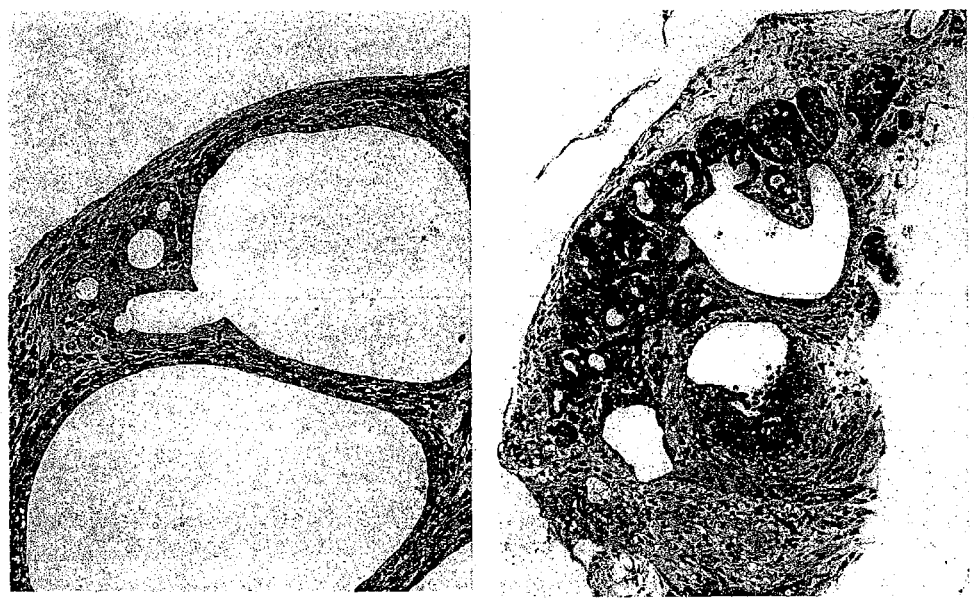
FIG. 6 is a photograph showing a pancreatic tissue including pancreatic duct, endocrine/exocrine cells and the like differentiated and induced from embryoid bodies by the method of Example 3.
Figure 7:
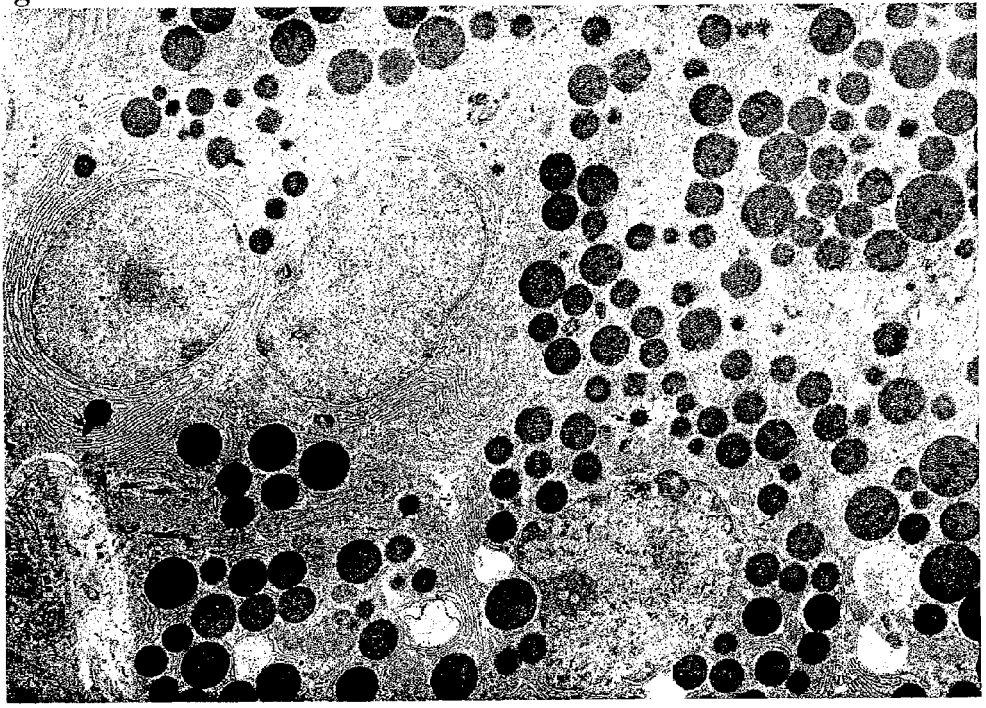
FIG. 7 is a photograph showing pancreatic exocrine cells induced by the method of Example 3.
Figure 8:
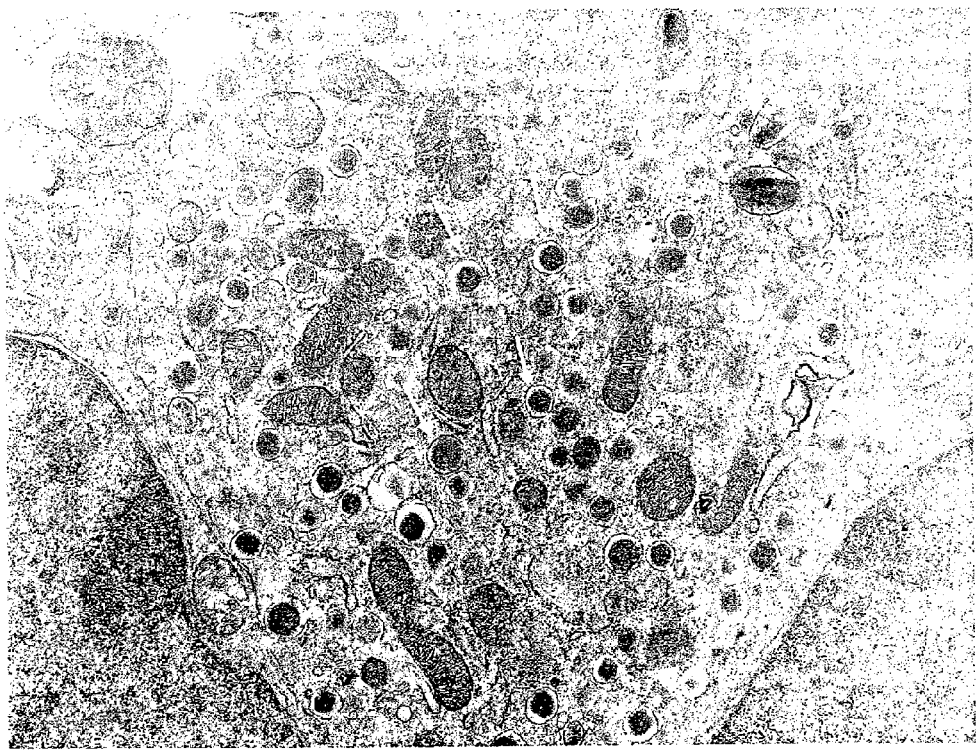
FIG. 8 is a photograph showing pancreatic β cells (endocrine cells) induced by the method of Example 3.

An intestine-like structure was induced and formed in 12 to 16 days of the culture (number of days from the start of EB formation). The induction and formation were observed in 60 to 70% of EBs treated with activin/Am80. Around the 21st day of the culture, a pancreas tissue-specific structure and specifically differentiated cells were formed in about 60% of the EBs in which the intestine-like structure was observed. In this pancreatic tissue, formation of a pancreas duct structure as well as morphology of many exocrine cells, including amylase secretory granules and endocrine cells producing insulin and glucagon, were observed. A photograph of the differentiated pancreatic tissue containing the pancreas duct and endocrine and exocrine cells induced from the embryoid bodies is shown in FIG. 6. FIG. 7 is a photograph showing induced pancreatic exocrine cells. FIG. 8 is a photograph showing induced pancreatic β cells (endocrine cells). Further, cultures were positive for anti-insulin antibody and anti-amylase antibody, and expressions of pancreas-specific transcription factors such as PDX-1, PAX-4, and NGN-3 were continuously observed in analysis by the RT-PCR method from 10th to 14th days of the culture.

INDUSTRIAL APPLICABILITY

The method of the present invention provides a means for forming a desired organ, for example, an organ such as a heart, nerve, pancreas or the like, from undifferentiated cells derived from a vertebrate animal.

What is claimed:

1. A method for forming pancreatic tissue from a mouse or human embryonic stem cell, which comprises culturing said embryonic stem cell to form an embryoid body; and culturing the embryoid body with 4-[(5,6,7,8-tetrahydro-5,5,8,8-tetramethyl-2-naphthalenyl)carbamoyl]benzoic acid and activin to form pancreatic tissue, wherein the pancreatic tissue formed includes pancreatic β cells and amylase secretory granules.

2. The method according to claim 1, wherein the embryonic stem cell is derived from a human.

3. The method according to claim 1, wherein the embryonic stem cell is derived from a mouse.

* * * * *